//1 United States Patent [19] [11] 4,143,649
Foti [45] Mar. 13, 1979

[54] PUMP FOR CLOSED CIRCULATION SYSTEM

[76] Inventor: George Foti, 1212 Port Washington Blvd., Port Washington, N.Y. 11050

[21] Appl. No.: 762,437

[22] Filed: Jan. 24, 1977

[51] Int. Cl.² .......................................... A61B 19/00
[52] U.S. Cl. ................... 128/2 N; 128/2 T
[58] Field of Search ............... 128/1 R, 2 N, 2.1 M, 128/2.05 F, 2 H, 214 A, 214 E, 9, DIG. 7, 409, 399–401, 2 T; 239/127; 15/346

[56] References Cited

U.S. PATENT DOCUMENTS

| 2,058,780 | 10/1936 | Elliott | 128/401 |
|---|---|---|---|
| 2,624,899 | 1/1953 | Smith | 401/13 |
| 3,017,885 | 1/1962 | Robicsek | 128/2.05 F |
| 3,460,538 | 8/1969 | Armstrong | 128/401 |
| 3,491,596 | 1/1970 | Dean | 128/2 H |
| 3,533,397 | 10/1970 | Scher | 128/399 |
| 3,545,428 | 12/1970 | Webster, Jr. | 128/2.05 F |
| 3,736,930 | 6/1973 | Georgi | 128/214 E |
| 3,789,853 | 2/1974 | Reinhard | 128/2 H |
| 3,830,234 | 3/1973 | Kopp | 128/214 E |
| 3,848,607 | 11/1974 | St. Clair | 128/400 |
| 3,942,515 | 3/1976 | Servos et al. | 128/2 N |
| 3,967,627 | 7/1976 | Brown | 128/400 |
| 3,978,850 | 9/1976 | Moore et al. | 128/9 |
| 3,995,621 | 12/1976 | Fletcher et al. | 128/2 H |
| 4,023,094 | 5/1977 | Adams | 128/2 H |
| 4,023,561 | 5/1977 | Servos | 128/2.1 M |
| 4,024,864 | 5/1977 | Davies et al. | 128/DIG. 7 |

FOREIGN PATENT DOCUMENTS 187217 10/1966 U.S.S.R. .................................. 128/1 R

OTHER PUBLICATIONS

Foti, T. M. et al., "A Closed-Flow Water Caloric System", Journal of the National Medical Assn., V.69 #5, 1977, pp. 303–305.
Ono et al, "A New Caloric Tester Using Ear Canal Balloon", Revue de Laryngologie, Otologie, Rhinologie, V.97 #5–6, May–June, 1976.

*Primary Examiner*—Robert W. Michell
*Assistant Examiner*—Francis J. Jaworski
*Attorney, Agent, or Firm*—Bacon & Thomas

[57] ABSTRACT

A hand-held portable pump has a self-contained reservoir to permit use for re-circulating flow applications. Reservoir liquid can be selectively heated or cooled and the flow rate can be selectively varied. The pump is operable in any orientation and is particularly suited for medical use wherein localized thermal transfer from the pump fluid to a patient is desired through a flow-conducting member. A specific embodiment, suitable for nystagmus inducing thermal transfer is disclosed. The pump is constructed so as to be readily carried in a pocket or instrument bag of a physician.

33 Claims, 11 Drawing Figures

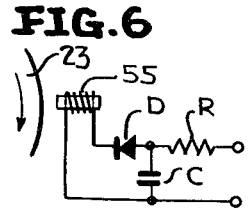
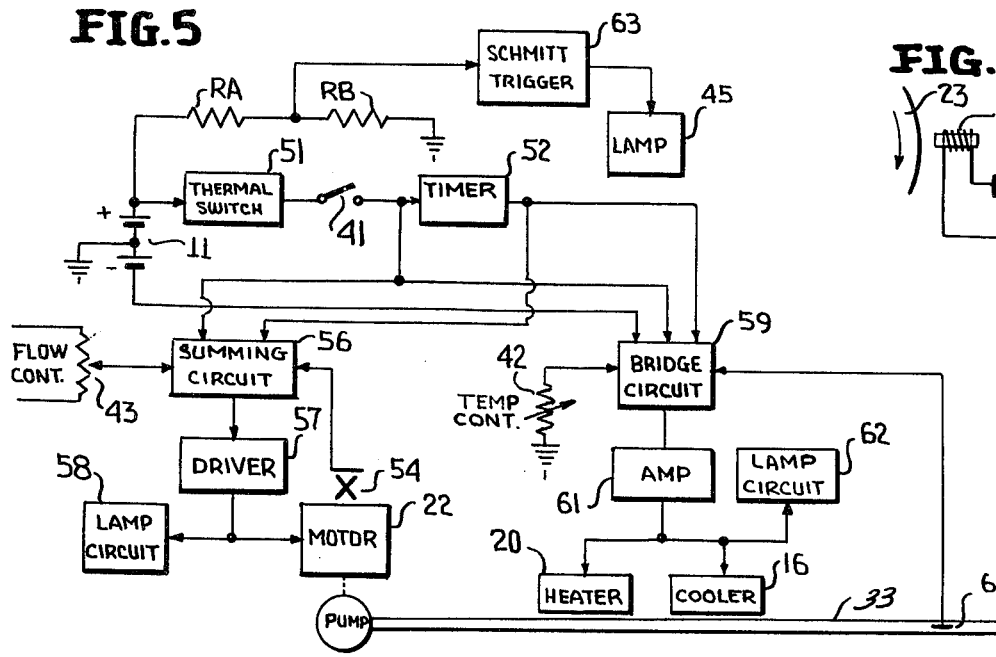
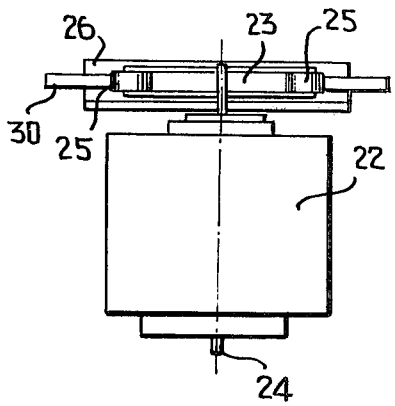
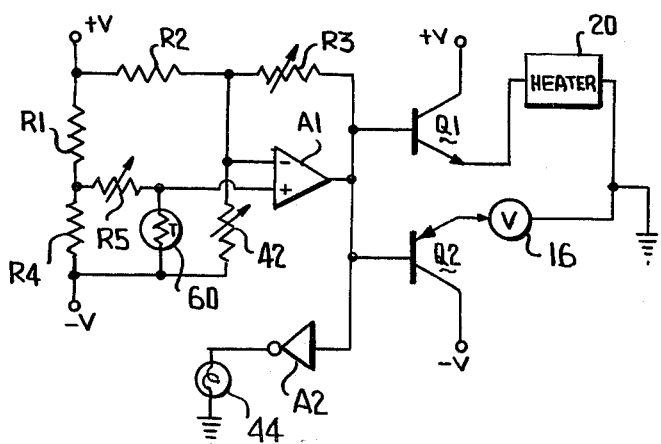
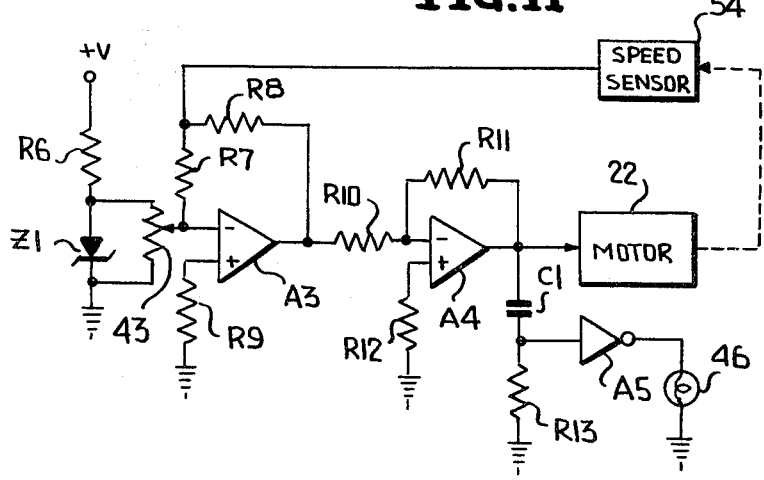

PUM P FOR CLOSED CIRCULATION SYSTEM

BACKGROUND OF THE INVENTION

The present invention relates generally to pumps and, particularly to hand-held pumps suitable for recirculation flow applications. More particularly, the present invention relates to pumps which may be utilized by the general physician to induce nystagmus. Although described herein as primarily suited for inducing nystagmus, the present invention will be understood as having considerably broader application wherever re-circulation flow from a pump containing its own reservoir is required.

Nystagmus, which is an involuntary movement of the eyeball, may be induced by temperature changes at the tympanic membrane in a patient's ear. By monitoring the movement of the eyeballs, a physician may readily diagnose various vestibular disorders. Typically, nystagmus is induced by issuing water or air at the desired flow rate and temperature directly into the patient's ear. Alternatively, in the so-called finger-cot method, fluid is issued into the open balloon-like member inserted in the patient's ear so that thermal transfer is effected through the balloon-like member. In all of these tests, the thermal fluid spills out of the ear so that a relatively large supply of liquid or a large air compressor is required.

A recent invention by Dr. Thomas M. Foti has eliminated the mess and waste of previous overflow techniques for inducing nystagmus. That invention involves the use of a closed ear probe containing a defined flow path and a thermal transfer surface. Thermal fluid is introduced through an inlet and caused to flow along the thermal transfer surface which is positioned adjacent the patient's tympanic membrane. The flow then egresses through a defined outlet. Such a probe permits a closed flow path with respect to the ear canal to be formed with attachment with a pump and thereby permits thermal fluid to be recirculated without spillage and waste.

This invention, which was made independently of the Foti probe, has advantageous use therewith. Specifically, I have developed a portable pump for attachment to the probe with which the system will become completely closed with regard to the external environment. In conjunction with the Foti probe this permits nystagmus testing to be performed anywhere by a general physician with no equipment other than the probe and pump. Heretofore, such tests could only be performed in an open water flow system directly in which the water was in direct contact with the ear canal and the eardrum.

It is therefore a primary object of the present invention to provide a highly sophisticated multi-parametrically adjustable pump which is suitable for use with the Foti probe to accomplish a true closed flow system not only within the ear canal but with external environment in a manner which will make caloric testing feasible for the general physician for screening and/or diagnostic purposes.

It is a further object of the present invention to provide a small portable pump capable of recirculating fluid stored in the pump at controlled rates of flow and controlled temperatures.

SUMMARY OF THE INVENTION

In accordance with the present invention a recirculation pump contains a reservoir of liquid, heating and cooling elements, a variable speed motor driving a pump assembly, controls for flow rate and temperature, and a re-chargeable battery. The entire unit fits in a shirt pocket or instrument bag and is operable in any positional orientation without disrupting the continuous closed flow pattern. Inlet and outlet connections are adapted to connect to respective outlet and inlet ports of the Foti probe.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein:

FIG. 5 is a functional block diagram of the pump of FIG. 1;

FIG. 6 is a schematic diagram of pump speed sensor;

FIG. 9 is a bottom view of the pump and motor assembly;

FIG. 10 is a schematic diagram of the temperature controller for the pump; and

FIG. 11 is a schematic diagram of the speed controller for the pump.

DESCRIPTION OF PREFERRED EMBODIMENT

Figure 3:
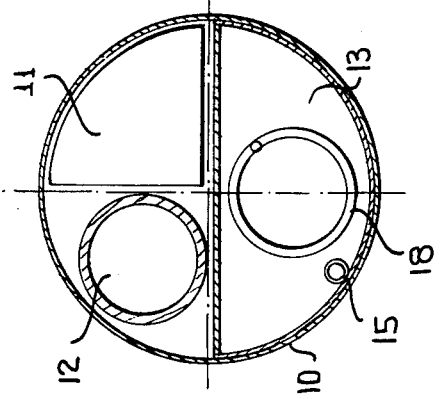
FIG. 3 is a view in section through lines 3—3 of FIG. 1.
Figure 4:
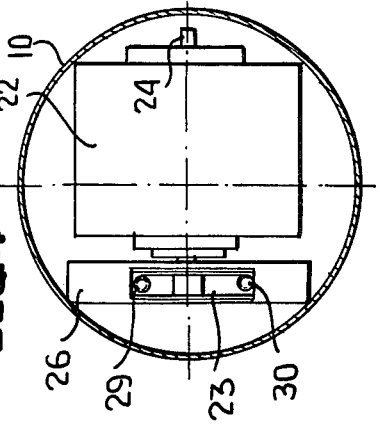
FIG. 4 is a view in section through lines 4—4 of FIG. 1.
Figure 2:
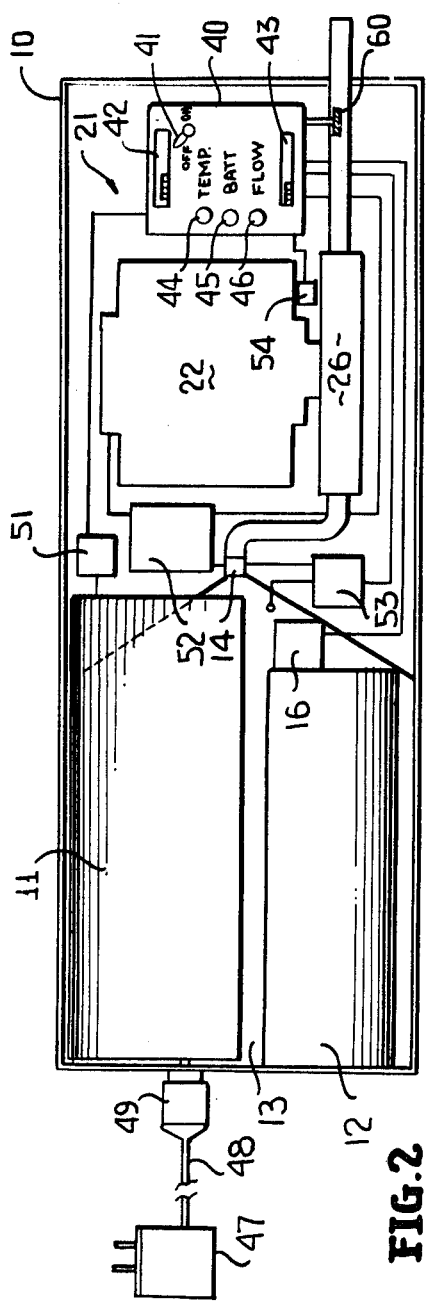
FIG. 2 is a diagrammatic top view of the pump of FIG. 1.

Referring in greater detail to FIGS. 1-9, the pump of the preferred embodiment of the present invention is located in a generally cylindrical housing 10 which is sufficiently small to be held or grasped in one hand. Typically, the housing is 20 cm long and 5 cm in diameter. It is to be understood that other configurations, such as rectangular in section, may be employed without departing from the inventive concept described herein. The important point is that the size and configuration permit complete portability and simple hand-held operation.

The rearward portion of housing 10 contains a rechargeable nickel-cadmium battery 11, a cartridge 12 of pressurized refrigerant and a thermal fluid (sometimes referred to as caloric liquid) reservoir 13 that is normally closed and fluid tight except for the fluid inflow and outflow openings to be described below. Looking rearwardly, battery 11 is in the upper right quadrant, cartridge 12 is in the upper left quadrant, and reservoir 13 in the two lower quadrants of the rear of housing 10. Cartridge 12 may contain carbon dioxide, a freon gas, or other similar coolant. Reservoir 13 is generally semi-cylindrical in shape except for a forward end which tapers upwardly and inwardly and terminates in an outflow pipe 14. An inflow pipe 15 extends from the rear of the reservoir interior out through the lower portion of the forward end of the reservoir.

A solenoid-actuated valve 16 is secured to the forward end of cartridge 12 and controls refrigerant flow out of cartridge 12 to tube 17. Tube 17 feeds a cooling conduit coil 18 disposed inside reservoir 13 in heat exchange relationship with the caloric liquid, and the coil terminates in an exhaust pipe 19 projecting rearwardly out through housing 10. The walls of reservoir 13 are formed of a resistive heating element 20. The heating element is sufficient to heat the thermal fluid in reservoir 13 to any temperature in the range 0°-60° C. Typically, the thermal fluid in reservoir 13 is water; however, it may be any of a variety of liquids.

Figure 1:
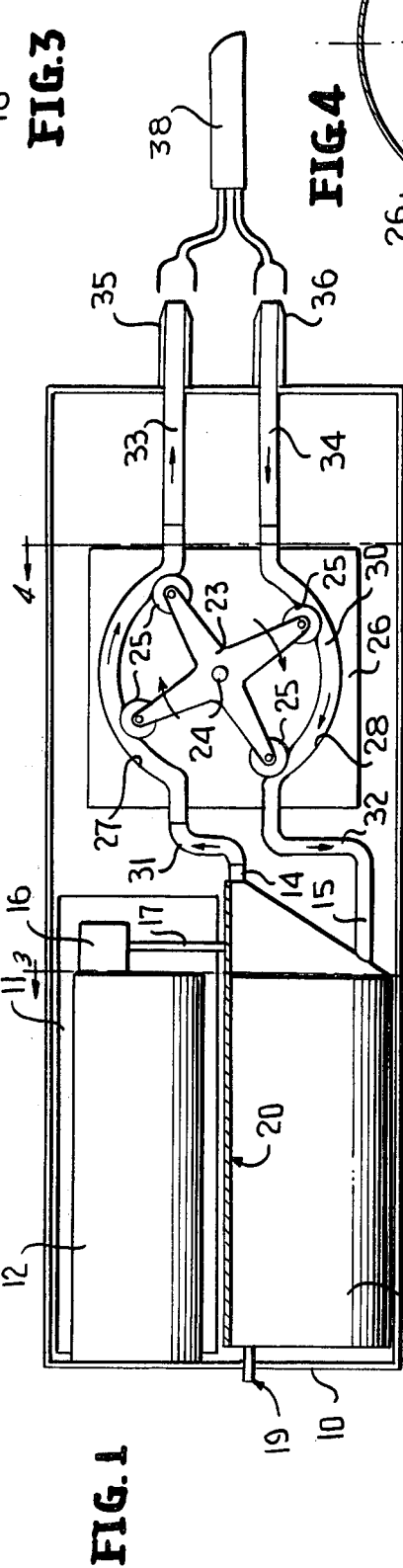
FIG. 1 is a diagrammatic side view of the interior of a pump according to the preferred embodiment of the present invention.
Figure 8:
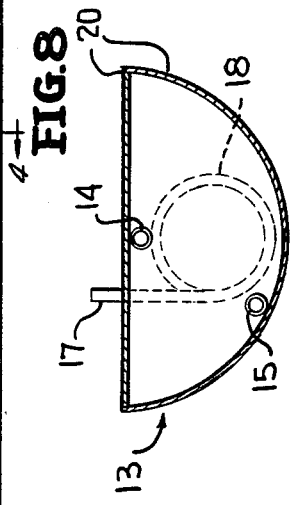
FIG. 8 is a front view of the liquid reservoir.
Figure 7:
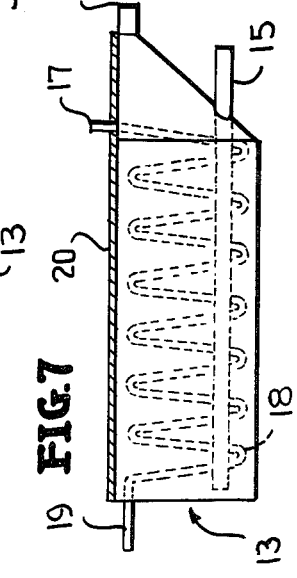
FIG. 7 is a side view of the liquid reservoir used in the pump of FIG. 1.

A motor and pump assembly 21 are disposed forward of elements 11, 12 and 13 in housing 10. A motor 22 rotates a drive shaft 24 to which a rotor 23 is connected in pump 26. The rotor 23 consists of a plurality of radial spokes which rotate in a space defined between diametrically opposed arcuate walls 27 and 28. A flexible outflow tube 29 is secured along arcuate wall 27 and a flexible inflow tube 30 is secured along arcuate wall 28. A roller 25 is pivotally mounted at the end of each rotor spoke and arranged to compress each of tubes 29 and 30 against walls 27 and 28, respectively, as rotor 23 rotates. This arrangement is the well-known peristaltic pump. Tubing 31 is connected between reservoir outlet tube 14 and the inlet end of pump outflow tube 27. Tubing 32 is connected between outlet end of pump inflow tube 30 and reservoir inflow tube 15. A further tube 33 is connected to the outlet end of pump outflow tube 29 and projects through the forward end of housing 10 where it is surrounded by an outlet fitting 35. A further tube 34 is connected to the inlet end of pump inlet tube 30 and projects out through the forward end of housing 10 where it is surrounded by an inlet fitting 36. As shown in FIG. 1, fittings 35 and 36 constitute inlet and outlet ports, respectively, which are adapted to fit into flexible inlet and outlet tubes of a closed flow thermal transfer device, such as the Foti probe 38.

A control section 40 is mounted on housing 10 and includes an on-off switch 41, a temperature setting control 42 and a flow rate control 43. In addition, lamp indicators 44, 45 and 46 are provided for temperature, battery and flow, respectively.

A conventional battery charger 47 can be connected by means of line cord 48 and plug 49 to the battery 11 to recharge the battery as necessary. A thermal safety switch 51, a timer 52, an amplifier 53 for heating element 20, and a motor speed sensor 54 are located within the housing 10 as part of the electrical circuit described below. The motor speed sensor 54 is illustrated schematically in FIG. 6 and includes a magnetic pick-up coil 55 located proximate rotor 23 to provide a pulse each time one of the rotor spokes passes by. An integrating circuit comprising diode D, capacitor C and resistor R is connected across coil 55 to provide a D.C. level representative of motor speed.

Operation of the system is best understood with reference to the functional block diagram of FIG. 5. D.C. power for the unit is supplied from battery 11 through protective thermal switch 51, on-off switch 41 and timer 52. The controlled power operates the motor speed control circuit and the temperature control circuit. The motor speed control circuit includes a summing circuit 56 which sums the fed back motor speed signal from speed sensor 54 with an operator-adjusted level at the speed control 43. The summing circuit output signal is amplified by driver circuit 57 to set the speed of motor 22. A lamp circuit 58 for lamp 46 is provided to yield a visual indication when the motor reaches constant speed.

The temperature control circuit includes a bridge circuit 59 of which temperature control 42 forms a part. In addition, a thermistor 60, located in outflow tube 33, forms part of the bridge circuit and provides resistance which is a function of the temperature of the thermal fluid and tends to force the bridge to a balanced condition. The bridge circuit 59 drives an amplifier 61 to provide a bi-polar signal which effects increased heating or cooling of the thermal fluid, depending on signal polarity and amplitude. A lamp circuit 62 for lamp 44 provides a visual indication of a constant thermal fluid temperature condition, as monitored by the bridge balance state.

The voltage from battery 11 is divided down by series-connected resistors RA and RB, the latter being adjustable to set a desired threshold level at the junction between the two resistors. A Schmitt trigger 63 is connected to the resistor junction and lights lamp 45 only when the threshold exceeds the set threshold. In this manner, the operator is apprised of a low battery voltage condition by virtue of lamp 45 being extinguished.

The temperature control circuit is illustrated in greater detail in FIG. 10. A resistive bridge circuit includes resistor R1 as a first leg connected to a positive supply voltage and resistor R2 as a second leg, also connected to the positive supply voltage. A third leg includes the temperature control potentiometer 42 connected between resistor R2 and a negative supply voltage. The fourth bridge leg includes thermistor 60 connected in series with a calibration potentiometer R5, the series combination being connected in parallel across a resistor R4; this leg is connected between resistor R1 and the negative voltage supply. An operational amplifier A1 has an inverting input terminal (−), connected to the junction between resistor R1 and potentiometer 43, and a non-inverting input terminal (+), connected to the junction between potentiometer R5 and the thermistor 60. A gain adjustment potentiometer R3 is connected between the output terminal of amplifier A1 and the inverting input terminal.

A PNP transistor Q2 has its collector connected to the negative supply voltage and its emitter connected to drive the solenoid-controlled valve 16, the solenoid being returned to ground. An NPN transistor has its collector connected to the positive supply voltage and its emitter connected to the reservoir resistive heater 20 which is returned to ground. The bases of transistors Q1 and Q2 are driven from the output terminal of amplifier A1, as is an inverter amplifier A2 connected to drive the temperature indicator lamp 44.

In operation, adjustment of the temperature control potentiometer 42 causes an unbalance in the bridge circuit, resulting in a voltage difference appearing across the input terminals of amplifier A1. This voltage difference has a polarity which is dependent upon the direction of change in potentiometer 42 and an amplitude which is proportional to the amount of such change. Depending upon the polarity of the signal, either transistor Q2 is switched on to operate solenoid valve 16 and permit coolant to flow through cooling coil 18 in reservoir 13, or transistor Q1 is switched on to pass current through the heating element 20 for the reservoir. Thermistor 60 responds to the heating or cooling of the thermal fluid by changing its resistance in a sense which tends to balance the bridge. When balance is achieved the voltage difference appearing across the amplifier input terminals is nulled and both transistors are switched off. If the temperature of the thermal fluid varies thereafter, the resistance of thermistor 60 changes accordingly, unbalancing the bridge, and switching on the appropriate transistor until the thermal fluid returns to the desired temperature setting (at control 42) as signified by thermistor 60 in restoring the bridge balance condition. When the bridge is balanced, the zero or low level output signal from amplifier A1 is inverted by inverter A2 to energize the temperature lamp 44. When the bridge is not balanced, the high level output signal from amplifier A1 is inverted to a low level to extinguish lamp 44.

The motor speed control circuit is illustrated in greater detail in FIG. 11. A pair of high gain amplifiers A3 and A4 each have inverting and non-inverting input terminals and an output terminal. The inverting input terminal of amplifier A3 is connected to the wiper arm of the speed control potentiometer 43 which in turn is connected across a zener diode Z1. This parallel combination is connected in series between ground and a resistor R6 which is in turn connected to the positive supply voltage. The combination of resistor R6, control 43 and zener diode Z1 provides a variable voltage divider having a range limited by the regulation action of the zener diode. The non-inverting input terminal of amplifier A3 is returned to ground through a resistor R9. A feedback path comprising the series combination of resistors R8 and R7 is connected between the output and inverting input terminals of amplifier A3.

The output terminal of amplifier A3 is resistively coupled through resistor R10 to the inverting input terminal of amplifier A4. The non-inverting input terminal of amplifier A4 is returned to ground through resistor R12. A feedback path comprising resistor R11 is connected between the output and inverting input terminals of amplifier A4. The output signal from amplifier A4 drives motor 22 at a speed proportional to the amplifier output signal. The motor speed is sensed by speed sensor 54 and a D.C. level proportional to that speed is fed back to amplifier A3 at the junction between resistors R7 and R8. The output signal from amplifier A4 is also passed to a differentiator circuit comprising capacitor C1 and resistor R13 connected in series between the output terminal of amplifier A4 and ground. The junction between C1 and R13 is connected to the input terminal of inverting amplifier A5 which drives the flow indicator lamp.

In operation, for any motor speed setting at control 43, the speed-proportional signal fed back from speed sensor 54 tends to maintain the motor at constant speed. When constant speed is achieved the output signal from amplifier A4 is at a constant level so that the differentiator circuit output level is low. This low level is inverted by amplifier A5 to actuate lamp 46. On the other hand, during motor speed changes the output level from amplifier A4 is changing, resulting in a high level output from the differentiator circuit. This high level is inverted to a low level by amplifier A5 to extinguish lamp 46.

It is clear that the temperature and flow controls 42 and 43 respectively, can be calibrated to permit reasonably accurate control over the temperature and flow rate of the thermal fluid. For use in inducing nystagmus, the readily accepted test temperatures of 30° C. and 44° C. may be specifically calibrated and indicated adjacent the control adjustment.

In operation with Foti probe 38, the probe is inserted in a patient's ear, either before or after the probe has been attached to the inlet and outlet fittings 36 and 35, respectively, of the pump unit. If the battery 11 is properly charged, as indicated by lamp 45, the unit may be operated under battery power. If not, the unit will operate during charging of the battery from the D.C. level transformed by charger 47 from standard convenience A.C. power. The on-off switch 41 is activated and the temperature control 42 is set to the desired temperature. Likewise, the flow control 43 is set to the desired flow rate. After the sixty second timer has cycled, the circuits of FIGS. 10 and 11 are energized and the desired flow rate and temperature are reached, as indicated by lamps 46 and 44. The pump delivers the thermal fluid to the Foti probe 38 via outlet tube 33 and receives return flow from the probe via inflow tube 34.

The pump is portable and compact and is easily held in one hand of an operator. It can be operated in any positional orientation over a wide controlled range of thermal fluid temperature and flow rates. Facility of use is increased by use of a rechargeable battery. A particular advantage of the pump when used with the Foti probe to induce nystagmus is the fact that the same thermal fluid can be re-used indefinitely for test after test and simply stored in the reservoir 13. The sealing action of rollers 25 against tubes 29 and 30 prevents leakage when the pump is not in use and isolates the ear probe from changes in pressure head of liquid caused by different elevations of the pump. In addition, suitable caps may be provided to seal off the inlet and outlet fittings to further assure against leakage when the pump is not in use.

A significant advantage of the pump of the present invention, when used as described with the Foti probe, is that it provides a convenient and inexpensive apparatus and method for inducing nystagmus. Heretofore, complex equipment has been required to provide open flow at controlled flow rates and temperature. The complexity and expense of such equipment has limited the use of nystagmus testing to specialists. The present invention brings the nystagmus testing within the capability of every general practitioner in the medical profession. Such practitioner can simply visually observe the nystagmus induced by the pump and probe and determine whether or not a vestibular problem exists. If such a problem does exist, the patient can be sent for further testing. Thus, the general practitioner can perform this simple and fast test on any patient who complains of dizziness and as part of any complete physical examination. There is no mess, no bulky equipment, and no anxiety induced in the patient.

Another significant advantage of the present invention lies in energy conservation. More particularly, prior art techniques of inducing nystagmus require large volumes of water (or air) because of the open flow approach practiced in the prior art. With the present invention the same small volume of liquid may be used continuously in a closed flow environment resulting in less water use and reducing heating requirements since the heated fluid is recirculated and need only be incrementally reheated.

While I have described and illustrated one specific embodiment of my invention, it will be clear that variations of the details of construction which are specifically illustrated and described may be resorted to without departing from the true spirit and scope of the invention as defined in the appended claims.

I claim:

1. A self-contained caloric liquid circulating system for use in a closed cycle, caloric nystagmus inducing system that includes an ear probe having caloric liquid inlet and outlet ports and a fluid flow path within the probe between the probe ports, comprising:

a hand-manipulable housing having caloric liquid inlet and outlet ports for communicating with said probe outlet and inlet ports respectively through suitable conduits, a caloric liquid reservoir for containing a supply of nystagmus inducing caloric liquid within the housing, the reservoir being normally closed except for liquid inlet and outlet openings, means providing communication between the housing inlet and outlet ports and the reservoir inlet and outlet openings, a pump for causing circulation of caloric liquid between the reservoir and the housing inlet and outlet ports, means located within the housing for driving the pump, means for normally positively preventing caloric liquid flow to or from the reservoir through the housing inlet and outlet ports when the reservoir contains caloric liquid and the circulating system is inoperative, temperature adjusting means within the housing for adjusting the temperature of the caloric liquid, said temperature adjusting means comprising means for cooling the caloric liquid, including a container of refrigerant material within the housing, a coolant conduit for carrying refrigerant in heat exchange relationship with the caloric liquid, and valve means for regulating the flow of refrigerant material through the coolant conduit.

2. Apparatus as recited in claim 1, said coolant conduit being associated with said reservoir for cooling caloric liquid within the reservoir.

3. Apparatus as recited in claim 2, wherein said refrigerant comprises a Freon.

4. Apparatus as recited in claim 2, wherein said refrigerant comprises carbon dioxide.

5. Apparatus as recited in claim 1, including means for adjustably preselecting a flow rate of caloric liquid, and means for automatically maintaining the preselected flow rate of caloric liquid delivered by said pump.

6. Apparatus as claimed in claim 1, wherein said housing has an elongated, generally cylindrical configuration and inlet and outlet ports are disposed at one end thereof.

7. Apparatus as recited in claim 1, including electrical means for automatically controlling said valve means for regulating the flow of refrigerant material.

8. Apparatus as recited in claim 1, said caloric liquid reservoir having sidewalls, and including resistance heating means located in at least one of the reservoir sidewalls for heating the liquid.

9. Apparatus as recited in claim 8, including electrical means for automatically controlling energization of said resistance heating means.

10. Apparatus as recited in claim 1, including automatic temperature selecting means associated with said temperature adjusting means, a first control for automatically maintaining the temperature of said caloric liquid constant at a preselected temperature; caloric liquid flow rate selecting means, and second control means for automatically maintaining the flow rate of said caloric liquid constant at a preselected flow rate.

11. For use in inducing nystagmus in a closed liquid flow system using a probe adapted to be inserted in a patient's ear, said probe having a liquid inflow connection, a liquid outflow connection, and an internal flow communication between said inlfow and outflow connections, a pump assembly comprising:

(a) a housing which is sufficiently small to be grasped within one hand of one treating the patient, said housing having an inlet and an outlet, (b) a reservoir located inside said housing and adapted to contain liquid to be pumped, said reservoir having an inlet and an outlet, (c) pumping means located inside said housing for pumping said liquid through said closed system wherein liquid is pumped, inter alia, from said reservoir outlet through said housing outlet and from said housing inlet to said reservoir inlet, (d) temperature adjusting means disposed within said housing for adjusting the temperature of said liquid, said temperature adjusting means including means for cooling said liquid, said cooling means comprising a container of refrigerant material positioned within said housing, a coolant conduit in heat exchange relationship with said liquid, means for providing flow communication between said container and said coolant conduit, and valve means for regulating the flow of refrigerant material through said coolant conduit, (e) said reservoir forming a normally closed liquid-tight container between said reservoir inlet and said reservoir outlet for preventing liquid flow in said housing other than via said reservoir inlet and outlet whereby said housing may be freely handled by an operator of said assembly in any orientation of said housing without spillage of said liquid from said reservoir into said housing, (f) means for preventing liquid flow from said reservoir inlet and outlet when said assembly is not in use, (g) said pumping means being secured within said housing and operable for pumping said liquid while said housng is hand-held, (h) means for connecting said housing outlet in flow communication with said inflow connection of said probe, (i) means for connecting said housing inlet in flow communication with said outflow connection of said probe, (j) said pump assembly adapted, in operation, to form a normally filled closed liquid flow system with said probe, and (k) said housing adapted, in operation, to be normally hand-held adjacent said patient's ear.

12. Apparatus as recited in claim 11 wherein said temperature adjusting means is operable to adjust the temperature of said liquid within the range of about zero degrees to about sixty degrees centigrade.

13. Apparatus as recited in claim 11 wherein said pumping means comprises first conduit means connecting said reservoir outlet to said housing outlet, second conduit means connecting said reservoir inlet to said housing inlet, at least one of a first pumping member positioned in or adjacent said first conduit means for pumping liquid from said reservoir out through said housing outlet and a second pumping member positioned in or adjacent said second conduit means for pumping liquid through said housing inlet ot said reservoir inlet.

14. Apparatus as recited in claim 11 wherein said pumping means comprises both said first pumping member and second pumping member.

15. Apparatus as recited in claim 11 wherein said pumping means further comprises electric motor means and means connected to said electric motor means for simultaneously and synchronously driving first and second pumping members.

16. Apparatus as recited in claim 15 wherein said first and second pumping members form part of a peristaltic pump.

17. For use in inducing nystagmus, a pump assembly as recited in claim 11 wherein said pump assembly further comprises a source of electrical power located within said housing and means for connecting said power source for operating said pumping means.

18. Apparatus as recited in claim 11, wherein said coolant conduit is associated with said reservoir for cooling liquid within the reservoir.

19. Apparatus as recited in claim 11, said refrigerant material comprising a Freon.

20. Apparatus as recited in claim 11, said refrigerant material comprising carbon dioxide.

21. For use in inducing nystagmus in a closed liquid flow system using a probe adapted to be inserted in a patient's ear, said probe having a liquid inflow connected, a liquid outflow connection, and an internal flow communication between said inflow and outflow connections, a pump assembly comprising:
   (a) a housing which is sufficiently small to be grasped within one hand of one treating the patient, said housing having an inlet and an outlet,
   (b) a reservoir located inside said housing and adapted to contain liquid to be pumped, said reservoir having an inlet and an outlet,
   (c) pumping means located inside said housing for pumping said liquid through said closed system wherein liquid is pumped, inter alia, from said reservoir outlet through said housing outlet and from said housing inlet to said reservoir inlet,
   (d) temperature adjusting means within said housing for adjusting the temperature of said liquid,
   (e) said reservoir forming a normally closed liquid-tight container between said reservoir inlet and said reservoir outlet for preventing liquid flow in said housing other than via said reservoir inlet and outlet, whereby said housing may be freely handled by an operator of said assembly in any orientation of said housing without spillage of said liquid from said reservoir into said housing,
   (f) said pumping means being operable for pumping said liquid while said housing is handheld, and said pumping means normally preventing flow of liquid between the reservoir and said housing inlet and outlet when the pump is inoperative,
   (g) means for connecting said housing outlet flow communication with said inflow connection of said probe,
   (h) means for connecting said housing inlet in flow communication with said outflow connection of said probe,
   (i) said pump assembly adapted, in operation, to form a normally filled closed liquid flow system with said probe, and
   (j) said housing adapted, in operation, to be normally hand-held adjacent said patient's ear.

22. Apparatus for inducing nystagmus, comprising, in combination:
   a probe adapted to be inserted in a patient's ear and having a liquid inflow connection, a liquid outflow connection, and an internal flow communication between said inflow and outflow connections, and
   a pump assembly comprising:
   a housing which is sufficiently small to be grasped within the hand of one treating the patient, said housing having an inlet and an outlet,
   a reservoir located inside said housing and adapted to contain liquid to be pumped, said reservoir being normally closed and liquid tight except for reservoir liquid inlet and outlet openings in communication with said housing inlet and outlet;
   temperature adjusting means located inside said housing for adjusting the temperature of said liquid,
   pumping means located inside said housing and operable for delivering liquid from said reservoir through said outlet and from said inlet to said reservoir,
   means for connecting said housing outlet in flow communication with said inflow connection of said probe,
   means for connecting said housing inlet in flow communication with said outflow connection of said probe, and
   said pumping means connected for preventing liquid flow from said reservoir when said pumping means is not in operation for arbitrary orientations of said housing.

23. Apparatus as recited in claim 22 wherein said pumping means comprises a single peristaltic pump having pumping means operable for positively pumping liquid out of said reservoir and into said reservoir.

24. Apparatus for inducing nystagmus in a closed liquid flow system comprising, in combination:
   (a) a probe adapted to be inserted in a patient's ear and having a liquid inflow connection, a liquid outflow connection, and an internal flow communication between said inflow and outflow connections,
   (b) a pump assembly comprising:
      (1) a housing which is sufficiently small to be grasped within the hand of one treating the patient, said housing having an inlet and an outlet,
      (2) a reservoir located inside said housing and adapted to contain liquid to be pumped, said reservoir having an inlet and an outlet,
      (3) pumping means located inside said housing for pumping said liquid through closed system wherein liquid is pumped, inter alia, from said reservoir outlet through said housing outlet and from said housing inlet to said reservoir inlet, said pumping means normally preventing flow of liquid between the reservoir and the housing inlet and outlet when the pumping means is inoperative,
      (4) temperature adjusting means secured inside said housing for adjusting the temperature of said liquid,
      (5) said reservoir forming a normally closed liquid tight container between said reservoir inlet and said reservoir outlet for preventing liquid flow in said housing other than via said reservoir inlet and outlet, whereby said housing may be freely handled by an operator of said apparatus in any orientation of said housing, (6) said pumping means secured within said housing and operable for pumping said liquid while said housing is hand-held, (7) means for connecting said housing outlet in flow communication with said inflow connection of said probe, and (8) means for connecting said housing inlet in flow communication with said outflow connection of said housing;

(c) said pump assembly adapted, in operation, to form a normally filled closed liquid flow system with said probe, and (d) said housing adapted, in operation, to be normally hand-held adjacent said patient's ear.

25. A self-contained caloric liquid circulating system for use in a closed cycle, caloric nystagmus inducing system that includes an ear probe having caloric liquid inlet and outlet ports and a fluid flow path within the probe between the probe ports, comprising:

a hand-manipulable housing having caloric liquid inlet and outlet ports for communicating with said probe outlet and inlet ports respectively through suitable conduits, a caloric liquid reservoir for containing a supply of nystagmus inducing caloric liquid within the housing, the reservoir being normally closed except for liquid inlet and outlet openings, means providing communication between the housing inlet and outlet ports and the reservoir inlet and outlet openings, a pump within the housing for causing circulation of caloric liquid between the reservoir and the housing inlet and outlet ports, said pump normally preventing flow of caloric liquid between the reservoir and said housing inlet and outlet ports when said pump driving means is inoperative, and means located within the housing for driving the pump, whereby the ear probe is normally isolated from the caloric liquid reservoir when the circulating system is inoperative.

26. Apparatus as claimed in claim 25, including:
caloric liquid temperature selecting means;
first control means for automatically maintaining the temperature of said caloric liquid constant at a preselected temperature;
caloric liquid flow rate selecting means;
second control means for automatically maintaining the flow rate of said caloric liquid constant at a preselected flow rate.

27. Apparatus as claimed in claim 25, including means for adjustably preselecting a temperature of said caloric liquid and control means for automatically maintaining the temperature of said caloric liquid constant at the temperature selected at said preselecting means.

28. Apparatus as claimed in claim 25, including means for adjustably preselecting a flow rate of caloric liquid, and means for automatically maintaining the preselected flow rate of caloric liquid delivered by said pump.

29. Apparatus as recited in claim 25, wherein said housing has an elongated, generally cylindrical configuration and said inlet and outlet ports are disposed at one end thereof.

30. The fluid circulating system recited in claim 25, said pump being adapted to isolate at least said housing outlet port from caloric liquid pressure head caused by a difference in elevation between the reservoir and the housing outlet port when the reservoir contains caloric liquid and the reservoir is raised above the said housing outlet port.

31. The fluid circulating system according to claim 25, said pump being located between the reservoir and the housing inlet and outlet ports.

32. Apparatus as recited in claim 25, including temperature adjusting means for adjusting the temperature of the caloric liquid, said temperature adjusting means comprising means for cooling said liquid, including a container or refrigerant material within said housing, a coolant conduit for carrying coolant from said container in heat exchange relationship with said liquid, and valve means for regulating the flow of refrigerant from said container to said coolant conduit.

33. Apparatus as recited in claim 32, said coolant conduit being associated with said reservoir for cooling liquid in the reservoir.

* * * * *